United States Patent [19]

Subramanian et al.

[11] Patent Number: 5,686,071
[45] Date of Patent: Nov. 11, 1997

[54] POLYMER AFFINITY SYSTEM FOR THE DELIVERY OF CYTOTOXIC MATERIAL AND OTHER COMPOUNDS TO SITES OF DISEASE

[75] Inventors: Ramaswamy Subramanian, Frederick; Fang Shi, Gaithersburg, both of Md.

[73] Assignee: Per Immune Holdings, Inc., Rockville, Md.

[21] Appl. No.: 471,264

[22] Filed: Jun. 6, 1995

[51] Int. Cl.$^6$ .................................................. A61K 39/44
[52] U.S. Cl. ..................... 424/179.1; 424/280.1; 424/487; 424/488; 430/15; 525/329.5; 525/329.7; 526/318.3; 530/391.1
[58] Field of Search .............................. 424/487, 280.1, 424/488, 179.1; 430/18; 525/54.1, 326.9, 329.5, 329.7; 526/318.3; 530/391.1

[56] References Cited

U.S. PATENT DOCUMENTS

| | | |
|---|---|---|
| 4,474,893 | 10/1984 | Reading . |
| 4,687,732 | 8/1987 | Ward et al. ................................. 435/6 |
| 4,722,899 | 2/1988 | Hamaoka et al. . |
| 5,395,688 | 3/1995 | Wang et al. . |

OTHER PUBLICATIONS

J.L. Klein et al., *Human Monoconal Antibodies: Application in Immunotherapy*, pp. 271–281, 1994.
D.J. Buchsbaum et al., *Antibody, Immunoconjugates and Radiopharmaceuticals*, 4:3:245–272, 1991.
S.P. Kramer et al., *J. Natl. Cancer Inst.*, 31:297–326, 1963.
S. Udenfriend et al., *Science*, 178:871–872, 1972.
T. Kaneko et al., *Bioconjugate Chem*, 2:133–141, 1991.
R. Julian et al., *Analytical Biochemistry*, 132:68–73, 1983.
G.L. Ellman, *Arch. Biochem. Biophys.*, 82:70 1959.
E. Tsuchida et al., *Makromol. Chem.*, 175:593–601, 1974 Abstract Only.
R. Subramanian et al., *Journal of Polymer Science, Polymer Chemistry Edition*, 22:437–451, 1984.
R. Subramanian et al., *Journal of Polymer Science, Polymer Chemistry Edition*, 17:1855–1860, 1979.
M. Haspel et al., *Cancer Res.*, 45:3951–3961, 1985.
R. Subramanian et al., *Bioconjugate Chem.*, 3:248–255, 1991.
G.A. Hawkins et al., *Cancer Research*, 53:2368–2373, 1993.
Gottstein et al 1994; Annals of Oncology 5 Suppl 1:597–103.
Davis et al *Microbiology* 3rd Ed. 1980. Ch. 7 Basis of Chemotherapy.
Seaver 1994 Genetic Engineering News vol. 14 No. 14 pp. 10 & 21.
Sevier et al 1981 Clin Chem vol. 27 No. 11: 1797–1806.
Maeda et al. 1984 J. Protein Chemistry vol. 3 No. 2 181–193.
Subramanian et al 1984 J. Polymer Science vol. 22: 478–479.
Han et al 1990 Makromol Chem Macro Symp. vol. 33:301–309.
Torchilin et al 1993 Proceed Inter Symp Control Rel. of Bioact. Mater vol. 22: 437–451.
Goodwin 1991 Antibody Conjugates and Radiopharmaceuticals vol. 4 No. 4 427–434.

*Primary Examiner*—Lila Feisee
*Assistant Examiner*—Julie E. Reeves
*Attorney, Agent, or Firm*—William M. Blackstone

[57] ABSTRACT

The use of interacting polymers and oligomers to selectively target compounds to desired sites, in-vitro and in-vivo, wherein the first polymer or oligomer is bound to a targeting agent and the second polymer or oligomer is bound to an active agent, such as a drug, a metal or a radioisotope.

3 Claims, 15 Drawing Sheets

CANCER SEEKING PROTEIN LINKED TO A POLYMER FRAGMENT (•)

RADIOLABELED POLYMER FRAGMENT THAT STRONGLY BINDS TO FRAGMENT (•)

Y INTERACTING FUNCTIONAL GROUP   ▯ RADIONUCLIDE

CANCER SEEKING PROTEIN LINKED TO A POLYMER
FRAGMENT (*)

RADIOLABELED POLYMER FRAGMENT THAT STRONGLY
BINDS TO FRAGMENT (*)

INTERACTING FUNCTIONAL GROUP      RADIONUCLIDE

POLYMER AFFINITY SYSTEM FOR THE DELIVERY OF CYTOTOXIC MATERIAL AND OTHER COMPOUNDS TO SITES OF DISEASE

This invention comprises the use of interacting polymers and oligomers to selectively target compounds to a desired site. We describe methods for preparing polymer coupled proteins and polymer coupled radiometal chelates. The interaction between these polymers and oligomers is confirmed by viscosity measurements.

BACKGROUND OF THE INVENTION

Antitumor antibodies have been successfully employed to diagnose tumors in patients. However, use of such antibodies conjugated to radioisotopes to treat tumors has not been demonstrated to be reliably effective in clinical studies. One of the major problems facing the radioimmunotherapists is the lack of significant uptake of radioactivity in the tumor. In several clinical studies involving cancer patients, it has been determined that the uptake of radioactivity in the tumor ranges from 0.001 to 0.00001% per gram of the injected dose. This, coupled with the fact that often there is high uptake of radioactivity in normal tissues, such as in the liver, spleen and kidney, has resulted in the development of multi-step targeting modalities for cancer treatment (2). They include the use of avidin/biotin, biotin/avidin/biotin combinations, receptor mediated targeting, bifunctional antibodies and enzyme conjugates (3,4).

According to our invention, which we call the zip-polymer approach, using interacting polymers and oligomers as affinity systems, the cytotoxic material is targeted to the tumor site with the help of polymer and oligomer conjugates: antibody-polymer/oligomer conjugate (MoAb-P1) and polymer/oligomer-ligand conjugates (P2-C), where MoAb represents the antibody, P1 and P2 represent the two interacting polymers/oligomers and C denotes the ligand, which may be a chelator, toxin, drug or other signal generating and/or cytotoxic material. For simplicity, when referring to polymers and oligomers in the following text and claims, the term "polymers" will be used.

Anticancer antibodies target tumor sites. By administering cytotoxic material coupled to antibodies one should easily kill cancer cells. However, in practice, due to other factors such as lack of affinity, specificity and high uptake in noncancerous tissues, the targeting ability of the antibody is often poor. In order to circumvent this problem, we chose interacting synthetic polymer pairs as reagents suitable for increasing the localization of the cytotoxic material to the desired site. These polymers interact with very high affinity for one another. One such polymer (P1) is attached to the antibody, which will carry the polymer to tumor site. Because of the affinity of antibody for the antigen containing tumor, the antibody will stay for a longer period of time at the tumor site than in other tissue. The other interacting polymer (P2) is attached to cytotoxic material. When administered, the polymer P2 will seek P1 and hence carry cytotoxicity to the tumor site. The polymer P2 that does not target the tumor site will clear from circulation rapidly because of its small size. Also, the uptake of cytotoxic materials in noncancerous tissues will be reduced because the cytoxic material is not directly attached to the antibody.

SUMMARY OF THE INVENTION

The present invention provides a novel approach to pre-targeting for imaging and therapy, wherein two interacting polymers are used to target cytotoxicity or radioactivity to a tumor site. The antitumor antibody is attached to one of the interacting polymers (MoAb-P1). The other polymer is covalently attached to a diagnostic or therapeutic entity, such as a radioisotope, cytoxic drug, a toxin or a combination thereof (P2-C). The invention also encompasses methods for the preparation of chelate coupled polymers, the preparation of polymer coupled antibodies without destroying the immunoreactivity of the antibody, using the interacting polymer pairs for targeting cytoxicity to desired sites and using macromolecular viscosity measurements to investigate the behavior of polymer complexation.

DETAILED DESCRIPTION OF THE EMBODIMENTS

In order to be effective, the antibody-polymer conjugate (MoAb-P1) should satisfy the following conditions:

1. Immunoreactivity: The polymer-antibody conjugate (MoAb-P1) must be essentially as immunoreactive as the unmodified antibody. One could alter the nature of the antibody (chain length, substituents and etc.) if necessary and achieve this.
2. The polymers (P1 and P2) should not react with endogenous compounds in circulation, if this material is to be useful for in vivo biological applications.
3. More than one polymer molecule can be attached to a protein. This in turn will increase the signal density.
4. If the polymer-antibody conjugate (MoAb-P1) is to be used for human administrations, the conjugate should not be immunogenic. This can be accomplished by the use of human monoclonal antibodies.

5. The antibody-polymer conjugate (MoAb-P1) should be stable in vivo long enough for targeting, binding the polymer-ligand and treating the target tissue with the active component. This can be tested under a variety of conditions (e.g., in serum).

The other interacting polymer strand is attached to the desired ligand pharmaceutical, such as a radiometal chelate conjugate (P2-C). In this case, the chelator can be attached to the polymer followed by the radiometal labeling of chelator coupled polymer. Alternately, depending on the characteristics of the radiometal, one can bind the radiometal first to the chelator and then attach the metal chelator to the polymer. Both of these preparations will have uses in biomedical applications.

The ligand (chelate, drug, toxin and etc.) attached polymer (P2-C) should possess the following characteristics:

1. The ligand-polymer complex P2-C must specifically bind to the polymer (P1) in the antibody-polymer conjugate (MOAb-P1) (specific recognition) after MoAb has localized in vivo.
2. The affinity of the antibody (or other targeting protein) must not be affected by the binding of the polymers.
3. The polymer ligand complex must have little or no affinity for normal tissues.
4. The volume of distribution of the radiometal bound polymer in the blood should be low compared with distribution in the target tissue. This will reduce the level of deposition of radioactivity in normal tissues, such as in blood, bone, liver, spleen, kidney and etc., a major problem associated with the use of radioimmunoconjugates and drugs.
5. The polymer-ligand complex must be stable under in vivo conditions (such as in serum).
6. The conjugate must have low immunogenicity, which may be accomplished by using relatively low molecular weight polymers (chain length 1–1000 units) All the above factors are taken into consideration prior to selecting the proper polymer pair.

Figure 1:
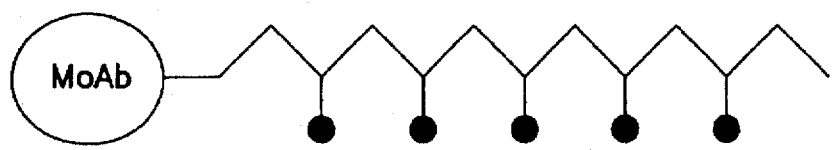
FIG. 1 illustrates the targeting moiety-polymer conjugate and the polymer-ligand complex, in an embodiment in which the targeting moiety is a monoclonal antibody and the ligand is a radionuclide.
Figure 1:
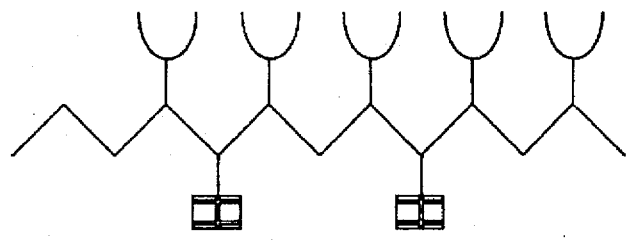
Figure 1:
Figure 1:
Figure 1:
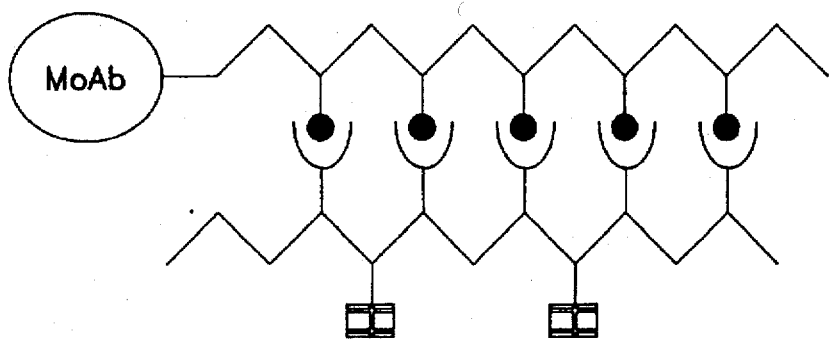

The use of interacting synthetic or naturally occurring polymers or oligomers, also called "zip polymers," are schematically represented in FIG. 1. Different pairs of polymers have already been described above. One or more of these polymers can be attached to desired materials, which include but are not limited to cytotoxic materials, such as drugs, pharmaceuticals, radioisotopes, isotopes useful for magnetic measurements, photochemically active materials, fluorescent materials, toxins, proteins, enzymes, abzymes, antibodies and other medically useful compounds. The isotopes that are useful for attachment include but are not limited to Tc-99m, In-111, Y-90, Re-186, Re-188, I-131, Sm-153, Cu-67, Pb-203, Bi-212, Bi-213, Ac-225, At-210, Ru-97, Co-57, Co-55, Cu-64, Cu-67, Ag-111, Hg-197 and Lu. The cytotoxic materials useful for linkage include but are not limited to bleomycin, anthracyclins, adriamycin, methotrexate, neocarcinostatin, 5-fluorouracil and other drugs. The toxins include but are not limited to pseudomonas toxin, cobra venom factor, barley toxin, ricin, diphtheria toxin, abrin, vinblastin and other endo/exotoxins.

Figure 2:
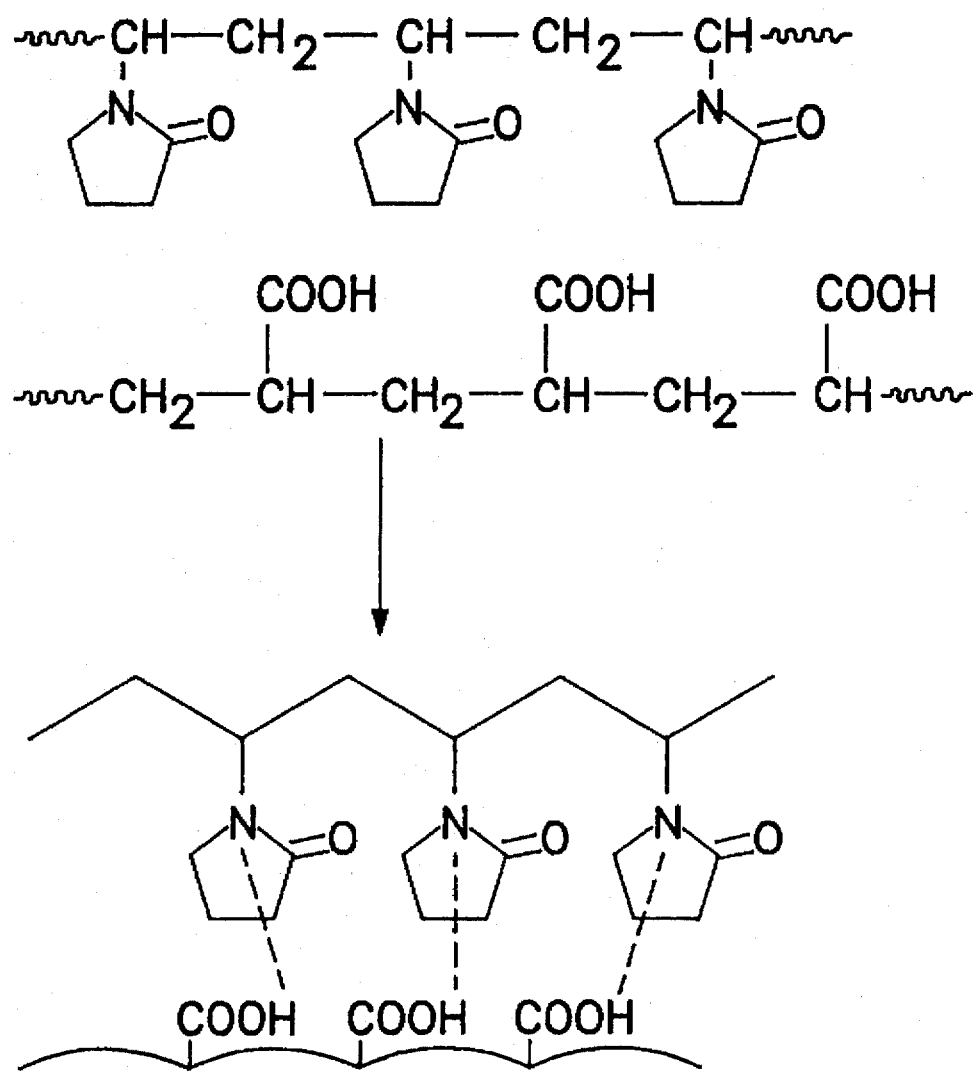
FIG. 2 illustrates polymer complex formation between Poly(N-vinyl pyrrolidone) and Poly(acrylic acid).

The polymers used in the invention are suitable for attachment to proteins such as monoclonal antibodies, polyclonal antibodies, enzymes, fragments of antibodies, F(ab') 2, F(ab'), oligonucleotides, other polymers, avidin, biotin and combinations thereof. One such pair of interacting polymer systems is poly(N-vinylpyrrolidone) (PVP) and poly(acrylic acids) (PAA), shown in FIG. 2.

This invention also comprises a novel method of synthesis of polymer-chelate conjugates, and the targeting of desired materials to the required sites employing affinity systems consisting of two or more synthetic polymers.

Interpolymer complexes are formed through secondary binding forces such as hydrogen bonding, Coloumbic interactions and van der Waals forces. Polymers such as poly (N-vinylpyrrolidone) and poly(acrylic acids) form inter polymer complexes. These interacting polymers include alginic acid and poly(vinyl alcohol), carboxymethylcellulose and poly(ethyleneoxide), cellulose and poly (vinylalcohol), carboxymethylcellulose and poly(vinyl alcohol), carboxymethylcellulose and polyvinylpyrrolidone, carboxymethyldextran and poly(ethylene oxide), dextran and poly(ethylene oxide), carboxymethyldextran and poly (propylene oxide), carboxymethyldextran and poly(vinyl alcohol), carboxymethyldextran and polyvinylpyrrolidone, dextran and polyacrylamide, dextran and poly(ethylene oxide), dextran and poly(vinyl alcohol), dextran and polyvinylpyrrolidone, poly (acrylic acid-Co-ethyl acrylate) and poly(vinyl alcohol), poly(acrylic acid-Co-maleic acid) and poly(ethylene oxide), poly(acrylamide) and poly (ethylene oxide), poly(2-dimethylaminoethyl methacrylate hydroacetate) and poly(methacrylic acid), poly(ethylene imine) and poly(methacrylic acid), poly(ethylene imine) and poly(acrylic acid), poly(ethylene oxide) and poly (methacrylic acid), poly(ethylene oxide) and poly (vinylpyrrolidone), poly(itaconic acid) and polyquaternary ammonium salts, poly(methacrylic acid) and polyquaternary ammonium salts, poly(acrylic acid) and polyquaternary ammonium salts, poly(methacrylic acid) and poly(vinyl alcohol), poly(methacrylic acid) and poly (vinylbenzyltrimethylammonium chloride), poly (methacrylic acid) and polyvinylpyrrolidone, poly (propylene oxide) and poly(vinyl alcohol), poly(propylene oxide) and polyvinylpyrrolidone, poly(styrenesulfonic acid) and poly(vinylbenzyltrimethylammonium chloride), poly (styrenesulfonic acid) and poly(4-vinyl-N-butylpyridinium bromide), poly(vinyl alcohol) and polyvinylpyrrolidone, poly(vinylamine hydrochloride) and polyvinylpyrrolidone, poly(vinyl sulfuric acid) and chitosan hydrochloride, poly (vinyl sulfuric acid) and trimethylammonium glycol chitosan iodide, and etc.

These interactive forces are strong enough to lead to the formation of precipitates when the concentration and the chain length of the polymer strands are sufficiently high (1). An increase in chain length increases the extent of binding. This phenomenon can be represented by the following equation:

$$k_a = k_1^a$$

where $k_a$ is oligomer binding constant, "a" is oligomer length, and $k_1$ is effective bonding constant of monomeric substance (with polymer molecule matrix). As clearly seen from this equation, the greater the length of the chain the greater the binding constant. However, increasing the chain length beyond a certain level increases the molecular weight of the polymer, which in turn will lead to an increase in the proportion of the material in the blood. The large size would inhibit clearance. This will result in relatively high dose deposition in normal tissues as well as in the blood. Hence, an optimum chain length is preferable, and this varies with the nature of the polymer. Preferred chain lengths will range from 1–1000 units. Other factors, such as pH, ionic strength of the medium, the nature of the medium, temperature and etc., will also influence the extent of interpolymer interactions.

The presence of such high interactive forces leads us to believe that when one of the interacting polymer strands (P1) is attached to a tumor targeting anti cancer antibody (MoAb) and the other interacting polymer strand (P2) is attached to a radioisotope, we can selectively target the isotope to the tumor site without having high non specific uptakes in normal tissues, such as the liver, spleen and kidney. This concept ("zip polymer" approach) is also applicable to conjugates containing cytotoxic materials such as toxins and drugs.

The following examples illustrate the invention, including the preparation of conjugates. Methods referred to in the literature are included herein by reference in their entirety.

EXAMPLE I

Materials 1-vinyl pyrrolidone/vinyl acetate copolymer (Mw 8,000) and poly(N-vinylpyrrolidone) (Mw 360,000) were purchased from Aldrich Chemical Co, Milwaukee, Wis., and purified by dissolution in methanol and precipitation in a 10 fold excess of diethyl ether. Poly(acrylic acid) (PAA, Mw: 5,000 to 90,000), poly(methacrylic acid) (PMAA, Mw 15,000), and poly(ethyleneimine) (PEI, Mw 10,000, 50000–100000) were purchased from Polysciences, Inc. and purified by dissolution in deionized water and precipitation in a 10 fold excess of acetone. Diethylenetrinaminepentaacetic acid dianhydride (DTPAa) was purchased from Sigma, St. Louis, Mo., and used without further purification. Dimethylformamide (DMF) was distilled over barium oxide under vacuum. Other reagents and solvents were purchased form Aldrich Chemical Company and used without purification.

Antibody

Recent studies have shown that peripheral blood lymphocytes obtained from cancer patients who had been immunized with irradiated autologous tumor cells mixed with BCG provide a good source of lymphocytes capable of producing tumor reactive antibodies (11). The B-lymphocytes producing the human monoclonal antibodies 88BV59 (ATCC CRL 10624) and 16.88 (ATCC HB8495) were obtained by this method.

88BV59 is an IgG3k antibody that recognizes a cytoplasmic antigen. Human monoclonal antibody 16.88 (IgM isotype) was produced by an Epstein-Barr Virus transformed human lymphoblastoid cell lines derived from peripheral blood lymphocytes. 16.88 also recognizes a cytoplasmic antigen.

Analytical Measurements

Proton NMR measurements were performed using a Varian 60 MHz NMR spectrometer. FTIR analysis was performed using a Perkin Elmer FTIR spectrophotometer. Mass Spectral analyses were performed at University of Minnesota according to our instructions. Elemental analyses were carried out by Atlantic Microlabs Corporation. C-13 NMR analyses were carried out at Chemir/Polytech Corporation.

Viscosity Studies

An apparatus for measurement of the viscosity of polymer solutions was constructed using the following components. YSI temperature controller, Model 72, Fisher Automerse Heater, Cylindrical water bath (glass), and Ubbelodhe viscometer (Fisher Scientific Supplies). The temperature of the water bath was maintained at 37°±0.05° C.

The viscosity of each component polymer or complex solution was measured at 37°±0.05° C., using the Ubbelodhe viscometer. Before each efflux time was measured, ten minutes were allowed for thermal equilibration. The efflux time for each component polymer or complex solution was noted as 't', and the efflux time for buffer was noted as '$t_0$'.

The specific viscosity was calculated ($n_{sp}$) according to the following formula:

$$n_{sp}=(t-t_0)/t_0$$

Synthesis and Characterization

Figure 3A:
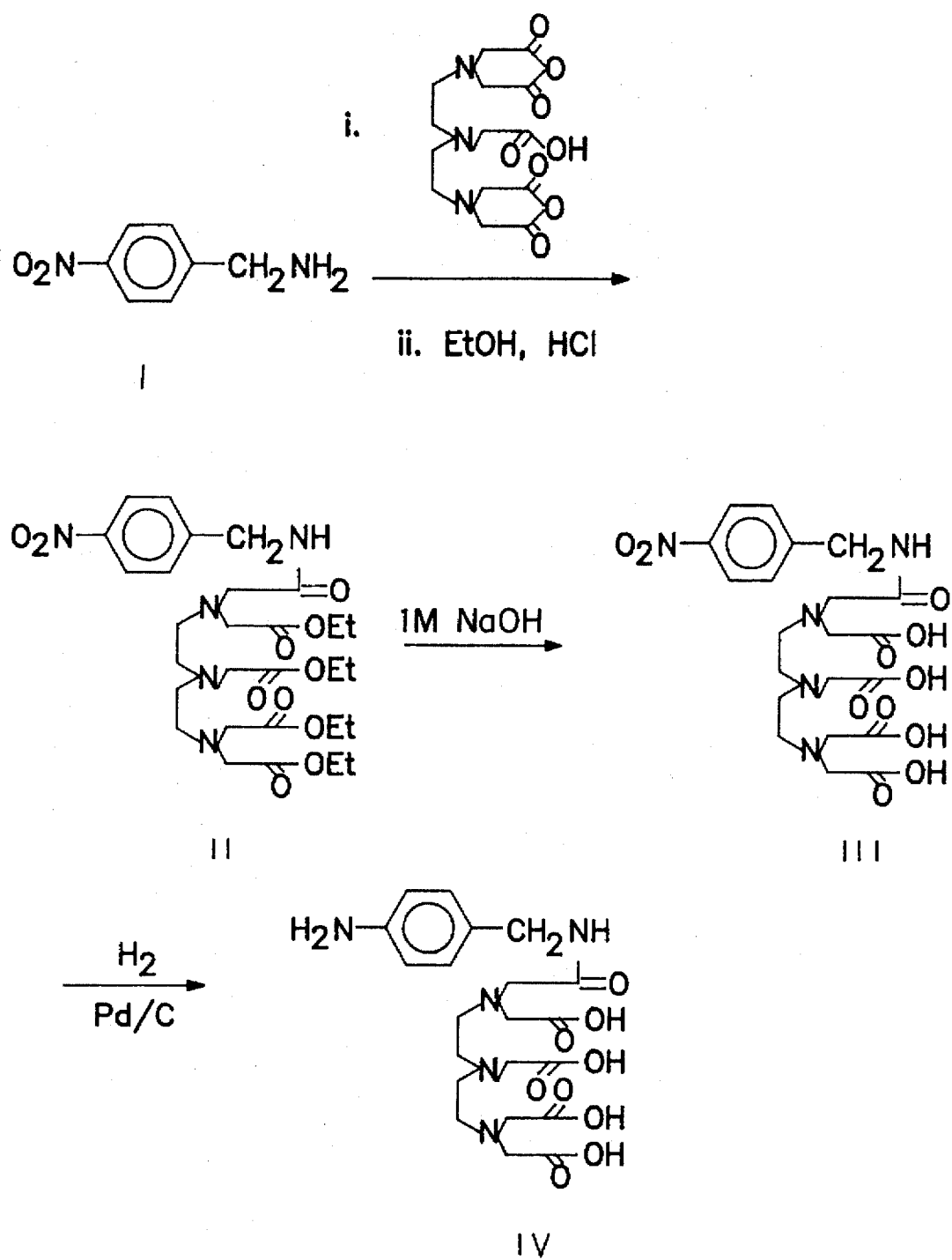
FIG. 3a illustrates the synthesis of 4-aminobenzylamine-DTPA (IV).
Figure 3B:
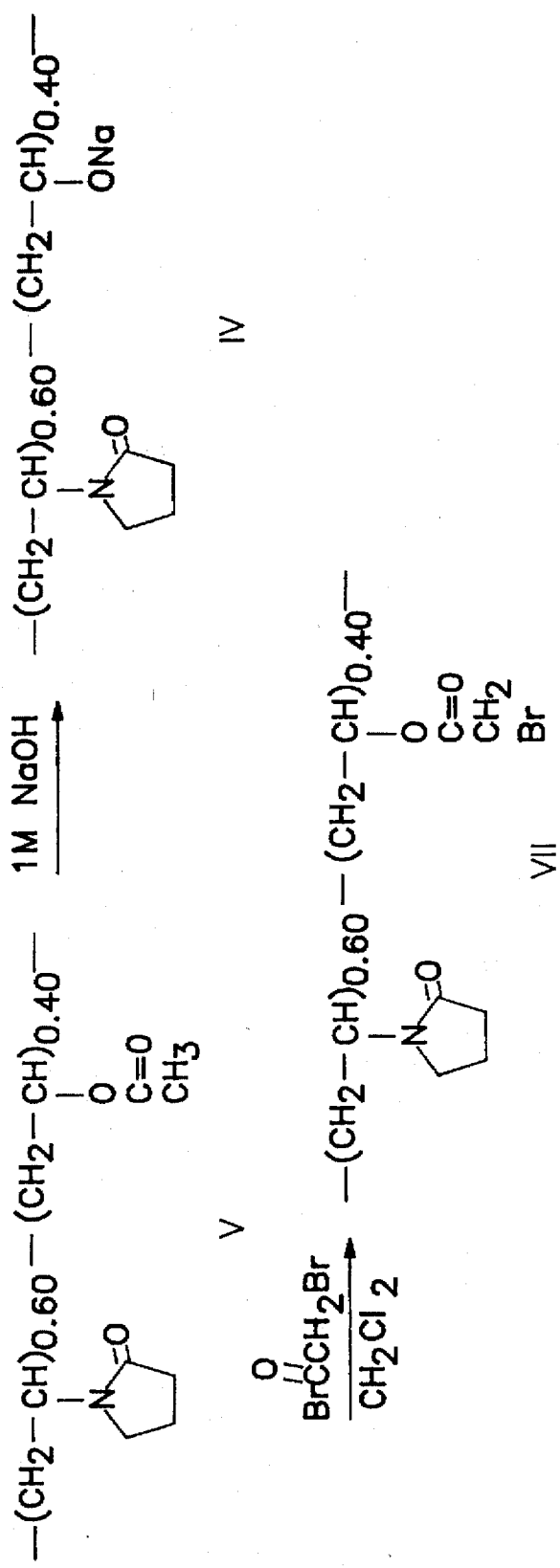
FIG. 3b illustrates the modification of vinyl pyrrilidone/vinyl acetate.
Figure 3C:
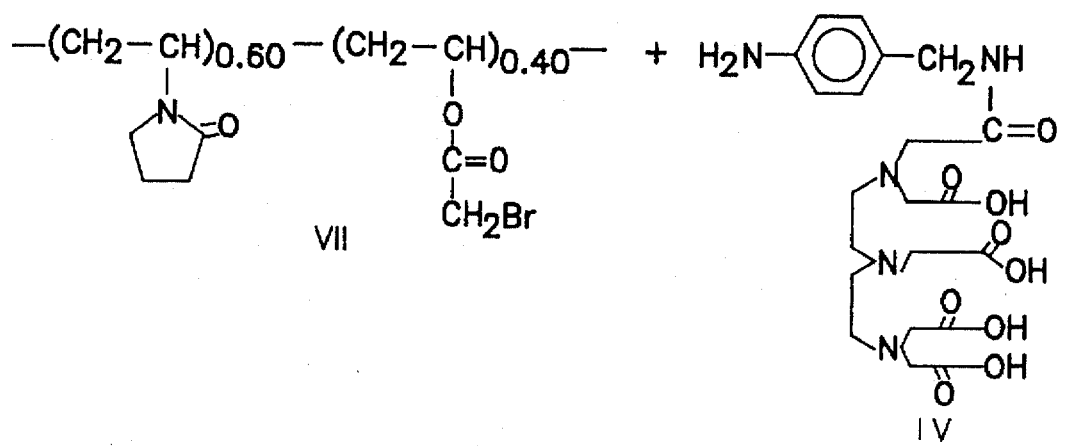
FIG. 3c illustrates the coupling of modified vinyl pyrrilidone/vinyl acetate with 4-aminobenzylamine-DTPA.
Figure 3C:
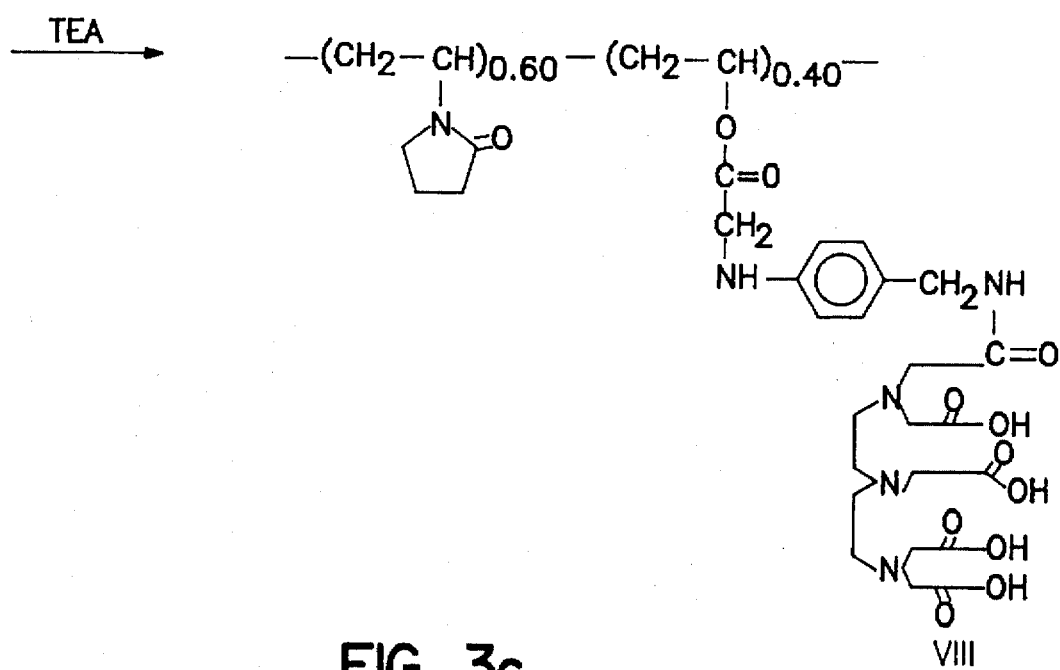
Figure 4:
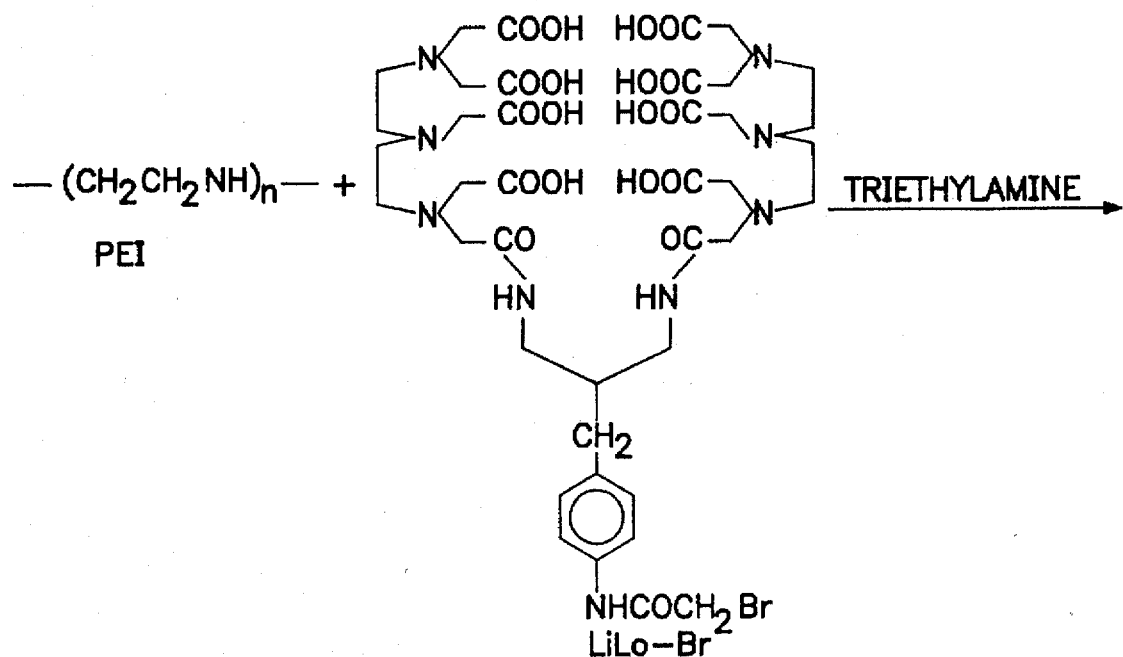
FIG. 4 illustrates the synthesis of PEI-LiLo.
Figure 4:
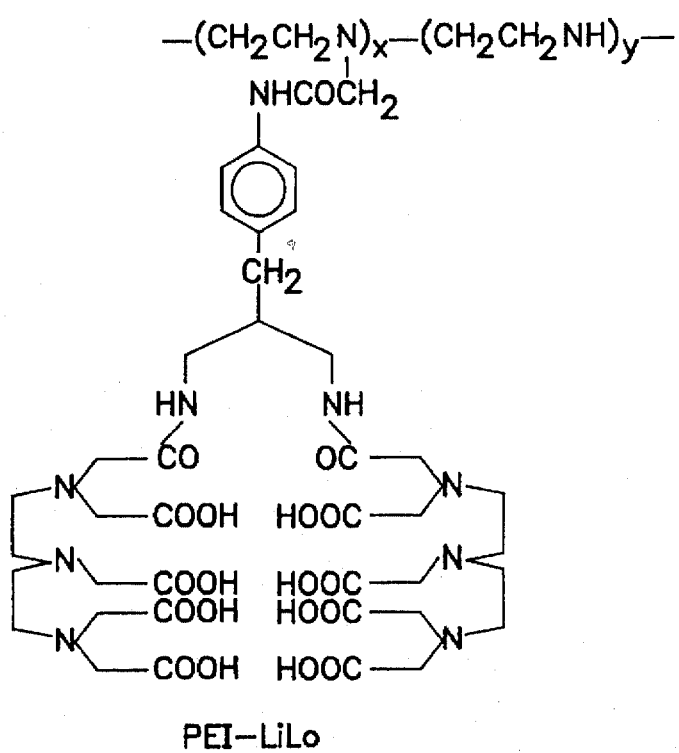

The synthetic scheme for the preparation of DTPA coupled poly(N-vinylpyrrolidone) PVP-DTPA is given in FIGS. 3a–3c.

Nitro Benzyl DTPA Ester (II)

Under nitrogen DTPAa (10 g, 28 mmole) was stirred into a solution containing 10 ml of triethylamine (140 mmole), 25 ml of acetonitrile and 15 ml of DMF. To the resulting suspension, 4-nitrobenzylamine hydrocholoride (I, 1.8 g, 3 mmole) was added in portions of 0.36 g every 2 hours with stirring. The reaction was allowed to proceed for 24 hours at room temperature after the final addition of 4-nitrobenzylamine hydrochloride. The solvents were evaporated under vacuum and absolute ethanol (250 ml) was added to the residue. The mixture was then saturated with HCl gas and refluxed overnight. The solvent was evaporated again. The residue was dissolved in saturated sodium carbonate solution at pH >9 and extracted with a mixture of hexane and ethyl acetate (3:1 v/v, 6 extractions of 150 ml each). The organic layer was dried over anhydrous magnesium sulfate, filtered, and evaporated. The resulting oil was purified by silica gel chromatography (0–5% methanol in methylene chloride) (1.41 g, 23%)

IR (KBr pellet): 2998.3, 1734.2, 1647.3, 1522.1, 1334.7, 1189.9 cm-1. TLC: Rf 0.44 (95:5 methylene chloride/methanol). 1H NMR (CDCl3) 8.3 (d, 2H); 7.5 (d, 2H), 4.1 (q, 8H); 3.5–3.2 (m, 12H); 2.8–2.6 (m, 8H); 1.2 (t, 12H). FABMS m/e (m+1) 640.4. Elemental analysis: Found (Calcd): C, 53.66 (54.45); H, 7.15 (7.09); N, 10.89 (10.95).

Synthesis of Nitro Benzyl DTPA-acid (III)

Nitrobenzyl DTPA ester (60 mg, 0.094 mmole) was mixed with 1M NaOH solution (0.14 ml, 0.56 mmole) and stirred at room temperature for 48 hours. The solution was then heated to 50°±2° C. for 12 hours, adjusted to pH 4-5 with 1M HCl solution, and then lyophilized to a yellowish powder. TLC Rf: 0.68 (80:20 methanol/ammonium hydroxide). IR (KBr pellet):3398.0, 2965.3, 734.6, 1684.0, 1519.5, 1419.0, 1349.0, 1254.4 cm-1. 1H NMR (D20) 7.9 (d, 2H); 7.1 (d, 2H); 4.2 (s, 2H); 3.1–2.3 (m, 18H). FABMS m/e (m+1): 528.4.

Synthesis of Amino Benzyl DTPA-Acid (IV):

Nitrobenzyl DTPA-acid (49 mg) was dissolved in 3 ml of deionized water and the solution was transferred to a Parr reaction vessel. To the solution a catalytic amount of 10% palladium/carbon was added. The resultant suspension was placed on a hydrogenation apparatus with a hydrogen pressure approximately 40 psi. The reaction was monitored by TLC (Rf-0.7, 80:20 methanol/ammonium hydroxide). The product was also found to be fluorescamine positive(6). IR (KBr pellet) 1738.2, 1678.8, 1566.2, 1404.9, 1210.6, 895.0 cm-1.

1-Vinyl Pyrrolidone/Vinyl Alcohol Copolymer (VI)

0.19 g (4.8 mmole) of sodium hydroxide was dissolved in 4.7 ml of methanol. The resultant solution was added to 800 mg of 1-vinylpyrrolidone/vinyl acetate copolymer (V). The mixture was stirred at room temperature for 48 hours. The hydrolyzed product, 1-vinyl pyrrolidone/vinyl alcohol copolymer was precipitated out in 10-fold excess of diethyl ether three times. The solid was then dried under vacuum at 60° C. overnight to yield 320 mg of 1-vinyl pyrrolidone/vinyl alcohol copolymer (VI). IR (KBr pellet): 3467.7, 2949.0, 1654.0, 1441.0, 1291.5, 649.9 cm-1: C-13 NMR, (D20) :17.6, 31.3, 33.6–35.1, 38.0–40.0, 42.6–45.9, 64.5–65.8.

5 1-Vinyl Pyrrolidone/Vinyl Bromoacetate Copolymer (VII)

A solution containing 330 mg of 1-vinyl pyrrolidone/ vinyl alcohol copolymer (VI) in 8 mL of dry dimethyl formamide was taken in a two-neck round-bottomed flask and connected to nitrogen. The other neck was capped with a septum stopper. The flask was cooled in an ice bath. To the flask 0.25 mL of bromoacetyl bromide dissolved in 2 mL of DMF was added dropwise with a syringe through the septum stopper. The reaction was allowed to proceed at room temperature for 1 hour in the dark. The precipitation of the reaction mixture in 15-fold diethyl ether for 5 times yielded 270 mg of 1-vinyl pyrrolidone/bromoacetate copolymer (VII). A test of alkylating agents using 4-(p-nitrobenzyl) pyridine was positive indicating the presence of alkyl bromide in the copolymer (5). C-13 NMR (CD3OD) : 19.2, 27.4, 32.5, 33.7–37.1, 43.6–45.5, 48.2–48.9, 70.0–71.5, 168.6, 177.7. Elemental Analysis: found (Calcd): C, 40.05 (43.5); H, 4.87 (5.11); Br, 30.97 (28.94); N, 5.43 (5.07).

Synthesis of PVP-DTPA (VIII)

Preparation of PVP-DTPA.In(111): Indium-111 labeling of PVP-DTPA was performed in citrate buffer solution, pH 5.5, at room temperature using procedures described in the literature (12a).

Serum Stability Studies

Figure 5:
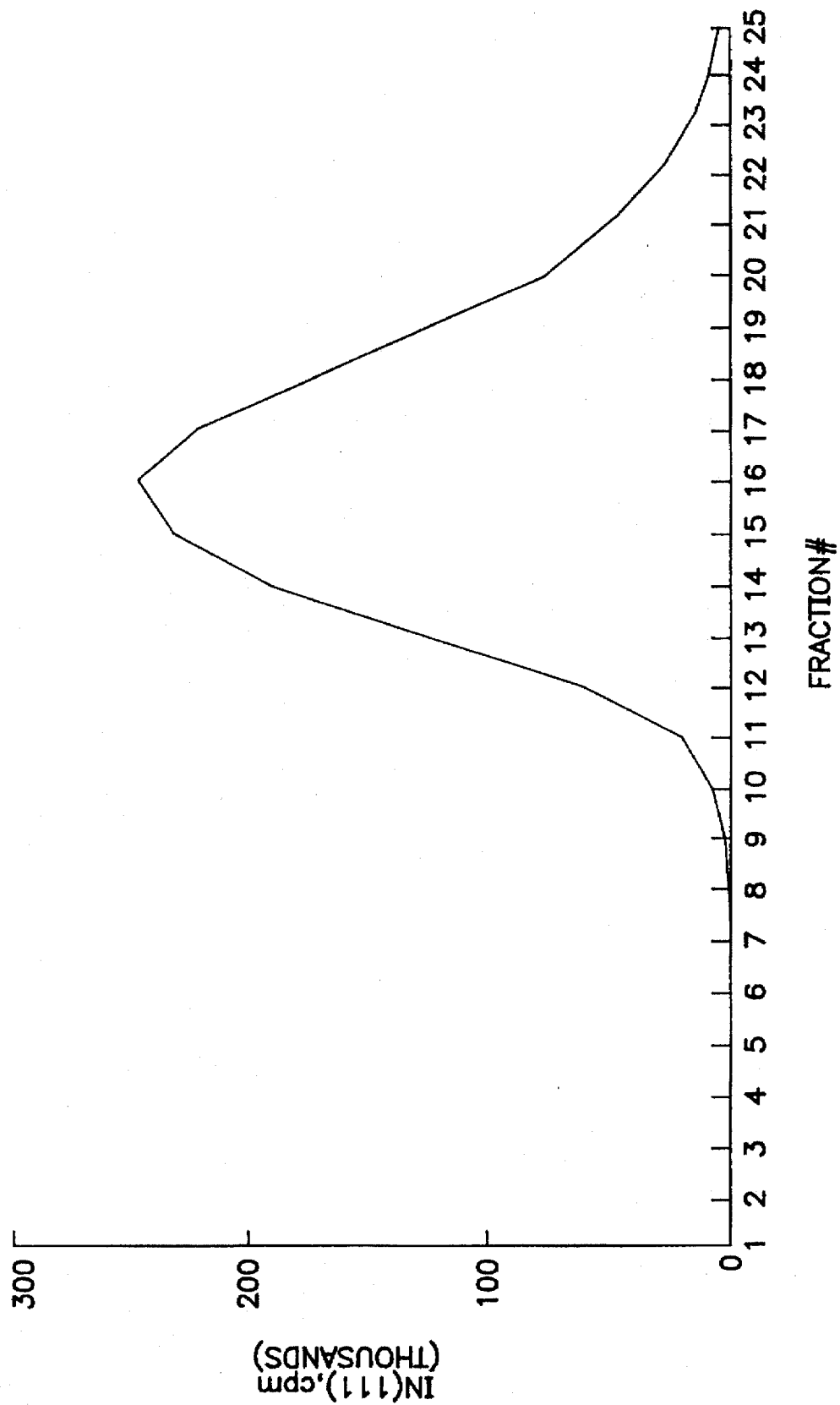
FIG. 5 is the gel filtration chromatogram of In(111) labeled PVP-DTPA, showing that the eluant was homogeneous.
Figure 6:
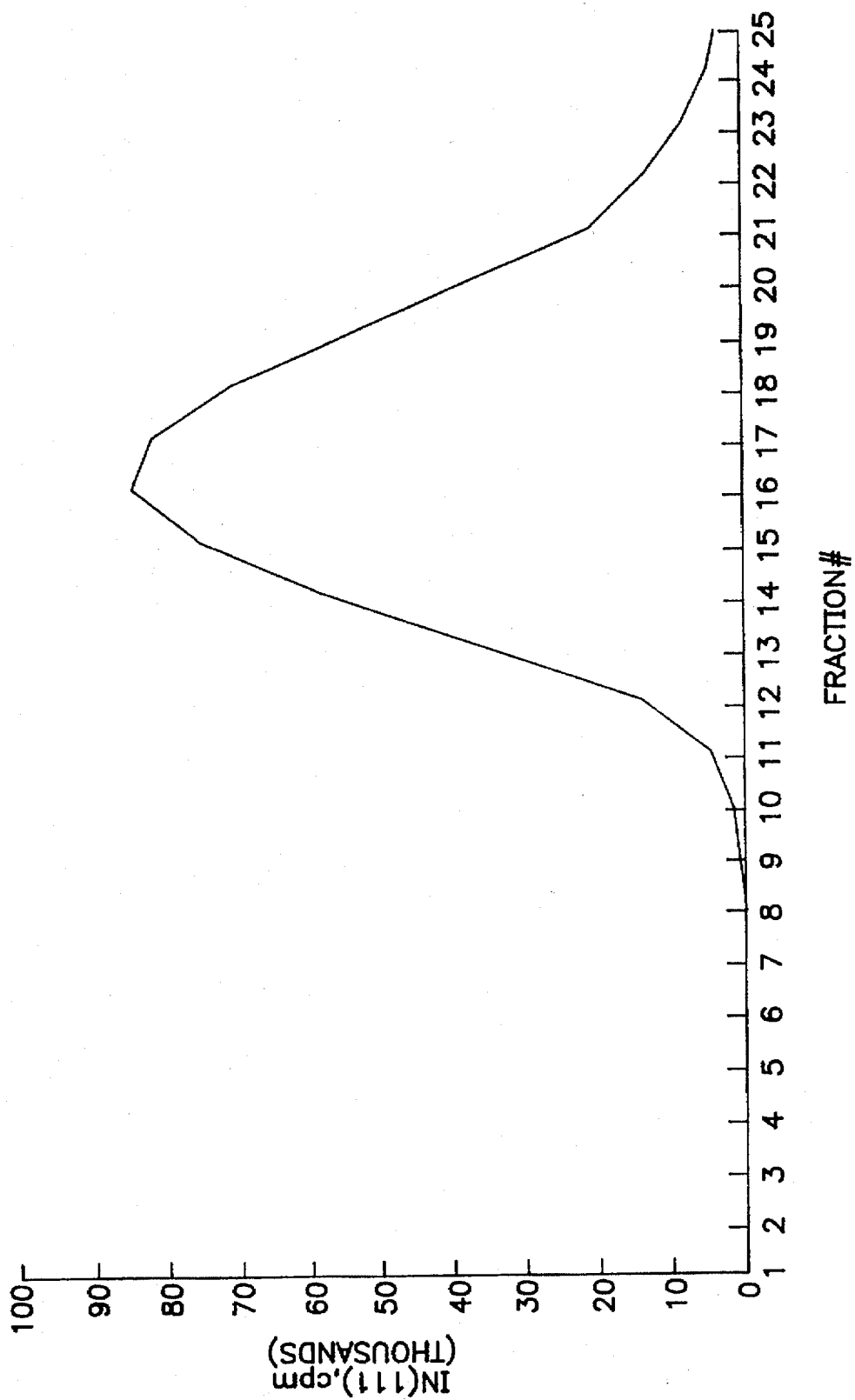
FIG. 6 is the gel filtration chromatogram of In(111) labeled PVP-DTPA in human serum, showing the lack of breakdown products in its homogeneity.

Serum stability studies were performed for indium-111 labeled PVP-DTPA. In(111) using procedures described elsewhere (12). An aliquot of serum containing indium-111 labeled PVP-DTPA was subjected to gel filtration chromatography and the radioactivity of each eluant fraction was determined. As shown in FIGS. 5 & 6, incubation in serum did not lead to the formation of any high molecular weight or low molecular weight species, indicating that PVP-DTPA.In(111) is stable in serum solution.

Conjugation of PAA to MoAbs

The conjugation of PAA to antibodies involves the preparation of modified PAA (PAA-PCA). PAA-PCA is then coupled to MoAb-SATA as described below.

1. PAA-PCA:
   A. Synthesis of 2-(2-pyridinyldithio)ethanamine hydrochloride: 2-(2-pyridinyldithio)ethanamine hydrochloride was synthesized as described in the literature (7). IR (KBr pellet) 3125.9, 2953.1, 2912.1, 1605.5, 1573.6, 1448.2, 1100.0, 869.6, 763.2 cm-1. 1H NMR (D20) 8.2 (d, 4H); 3.1 (m, 4H). TLC, Rf 0.24 (methanol/ methylene chloride 20:80 v/v).
   B. Synthesis of PAA-PCA: Polyacrylic acid (PAA, Mw: 5000, 300 mg, 4.6 unit mmole) was dissolved in 2 ml of deioinzed water and 1-hydroxybenzotriazole (140 mg, 1.04 mmole) in 0.5 ml of DMF. The above two solutions were mixed with stirring followed by the addition of s-pyridylcysteamine hydrochloride (PCA) in 2.5 ml of dimethylformamide. The pH was adjusted to 6.5 with triethylamine. To the solution 1-(3-dimethyl aminopropyl)-3-ethylcarbodiimide, hydrochloride (192 mg, 1 mmole) was added with stirring to form a clear yellowish solution. The reaction was allowed to proceed at room temperature for approximately 19 hours. The solution (5 ml) was then loaded on a Sephadex G10 column (1.5×39 cm) and eluted with phosphate buffer (50 mM, pH 7.5). The UV spectra of the fractions were taken, and the ones showing absorption peaks at 234 and 282 nm were collected and stored at −70° C.

Figure 7:
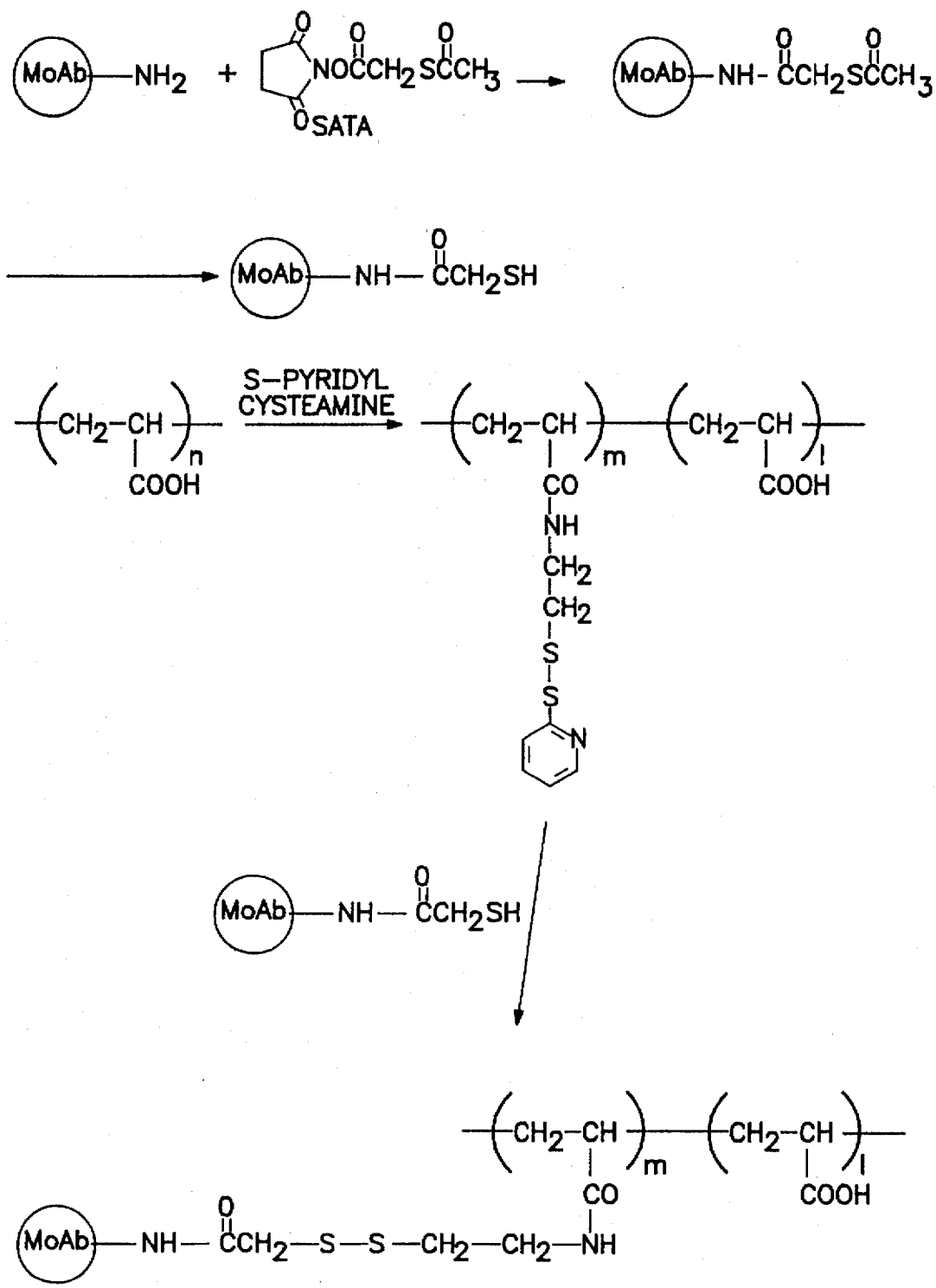
FIG. 7 illustrates the coupling of MoAb to PAA.

2. Conjugation of PAA to MoAb:

The conjugation of PAA to 88BV59 and/or 16.88 consists of two parts (FIG. 7). First the antibody is activated with N-succinimidyl S-acetylthioacetate (SATA) groups (8). This is followed by the attachment of derivatized PAA groups (PAA-PCA). A typical modification procedure is as follows:

A. Modification of MoAb: 88BV59:4 ml of 88BV59 (50.64 were mixed with 40 uL of SATA in dimethyl sulfoxide (13.6 mg/mL). The resultant solution was kept on a slow rotator for 30 minutes, then loaded on a Sephadex G50 column (19×3 cm) and eluted with phosphate buffer (50 mM, pH 7.5) containing 1 mM EDTA. The first group of fractions showing absorption at 280 nm were collected to yield 6 ml of 88BV59-SATA conjugate (20 mg).

Figure 8:
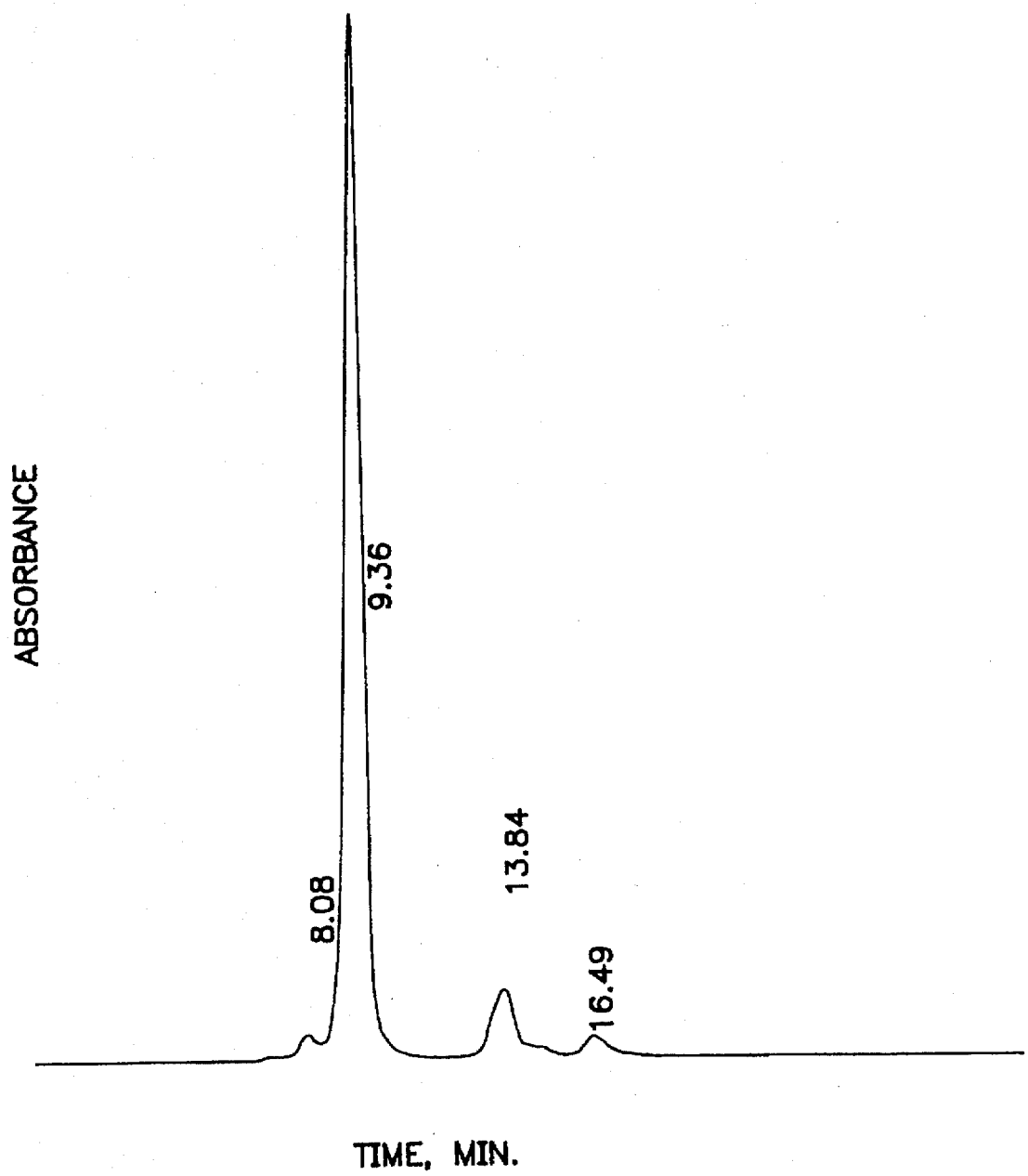
FIG. 8 illustrates the HPLC chromatogram of 88BV59-PAA.

B. Coupling of PAA-PCA to 88BV59-SATA: To 6 ml of 88BV59-SATA conjugate solution prepared above was added 200 uL of 0.5M hydroxylamine hydrocholoride in phosphate buffered solution (pH 7.2) containing 25 mM EDTA. This deacetylation reaction was allowed to proceed at room temperature for 30 minutes. The number of sulfhydryl groups post deacetylation was found to be approximately 6 per antibody molecule with Ellman's reagent. To the deacetylated solution 70 uL of PAA-PCA (Mw 5000, 6.7 mg) was added. The resultant solution was kept on a slow rotator for 1.5 hours before it was loaded on a Sephadex G50 column (2.5 cm×19 cm) and eluted with phosphate buffer, 50 mM (pH 7.5) containing 1 mM EDTA. The first peak was collected (as measured by absorption at 280 nm) to yield 16 mg of 88BV59-PAA conjugate. The HPLC data (gel filtration chromatography using BioSep SEC 3000 column) showed that the polymer conjugate 88BV59-PAA is essentially pure, eluting as a single peak at 9.36 min (FIG. 8). 16.88: 16.88-SATA conjugate was prepared in the same way as in the case of 88BV59-PAA. 16.88 (98.4 mg, 0.109 µmole) was modified with SATA (0.76 mg, 3.27 µmole) and purified. 16.88-SATA (31.8 mg, 0.035 µmole) was deacetylated and reacted with PAA-PCA (3.53 mg, 0.71 µmole) to yield 23 mg of 16.88-PAA. The number of PAA per 16.88 was found to be 8.6 as per Ellman's test (9).

The interacting polymer (P1) can be coupled to antitumor antibody using methods well known in the art. Homobifunctional and/or heterobifunctional linkers can be used to attach P1 to the antibody. These linkers include but are not limited to bismaleimidohexane, bis(sulfosuccinimidyl)suberate, bis [2-(succinimidoxoycarbonyloxy)ethyl]sulfone and its analogs, 1-5-disflouro-2,4-dinitrobenzene, dimethyl adipidate, dimethyl pimelimidate, dimethyl suberimidate, 1,4-di[3'-(2'-pyridyldithio) -propionamido)]butane, disuccinimidyl glutarate, dithio bis (succinimidyl propionate), disuccinimidyl suberate, disuccinimidyl tartarate and its analogs, dimethyl(3,3'-dithiobispropionimidate), dithiobis (sulfosuccinimidyl propionate), EDC or 1-ethyl-3-(3-dimethylaminopropyl)carbodimide hydrochloride, ethylene glycol bis(succinimidyl succinate), N-υ-maleimidobutyryloxysuccinimide ester, photoreactive linkers such as N-hydroxy succinimidyl 4-azidobenzoate, N-hydoxy succinimidyl 4-azidosalicylic acid and analogs, other azido derivatives suitable for coupling to proteins, m-maeimidobenzoyl-N-hydroxysuccimide ester and its analogs, 4-(maleimidophenyl)-butyric acid hydrazide.HCl, 3-(2-pyridyldithio)propionyl hydrochloride, (N-hydroxy succinimidyl)2,3-dibromopropionate, N-succinimydyl (4-iodoacetyl)aminobenzoate, succinimidyl 4-(N-maleimidomethyl) cyclohexane-1-carboxylate, succinimydyl 4-(p-maleimidophenyl) butyrate, 4-succinimidyloxycarbonyl-α-(2-pyridylthio)toluene, and N-succinimidyl-3-(2-pyridyldithio)-propionate and its analogs are some of the representative linkers useful for attaching polymer strands to proteins such as monoclonal antibodies. These cross-linking reagents can be purchased from commercial vendors such as Pierce, Aldrich, and Sigma. Methods for attaching these linkers to proteins are described in the art. These reagents can also be used for attaching cytotoxic materials such as radiometal chelates, drugs and toxins to the other interacting polymer(P2).

Immunoreactivity of 88BV59-PAA

The attachment of the polymer PAA to the human monoclonal antibody 88BV59 did not significantly affect the immunoreactivity of the antibody. This was confirmed by determining the immunoreactivity of technetium-99m labeled 88BV59-PAA conjugate.

Technetium-99m Labeling of 88BV59-PAA

Technetium-99m labeled 88BV59-PAA was obtained as follows. To a solution of 88BV59-PAA (0.3 mL, 2.8 mg/mL), 0.2 mL of stannous saccharate solution was added. Stannous saccharate solution was prepared by combining approximately 250 μg stannous chloride and 500 ug saccharic acid. The reaction mixture containing 88BV59-PAA was incubated at 37° C. for about 1 hr. Sodium pertechnetate (Tc-99m) solution purchased from DuPont-New England Nuclear Corporation (0.05 mL, 14 mCi) was added to the reaction mixture. The incubation at 37° C. was continued for additional 30 minutes. At the end DTPA solution (0.2 mM in 0.1M sodium bicarbonate) was added to the mixture to scavenge any unbound and/or loosely bound Tc-99m. After leaving the reaction mixture at room temperature for about 5 minutes, 0.4 mL of saline solution was added to the mixture. The solution was then poured over a PD-10 gel filtration column (Pharmacia) and eluted with saline solution. The radioactivity of the eluant fractions was determined using a CRC-7 radioisotope detector (Capintec Corporation). The fractions present in the first radioactive peak were pooled together. The radiochemical purity of the radiolabeled antibody present in the first peak was determined by an instant thin layer chromatography procedure (ITLC) using 0.1M sodium acetate solution (pH 5.0) as the chromatography buffer and Gelman ITLC-SG chromatography sheets. The ITLC analysis indicated that 97.9% of technetium-99m was bound to the antibody.

Immunoreactivity of technetium-99m labeled 88BV59-PAA was determined using an affinity column assay making use of an antigen (CTA-1) coated sepharose bead column. The immunologically reactive part of the radiolabeled antibody solution will stay bound to the affinity column and the remaining material simply comes off the column when washed with a phosphate buffer solution. By determining the radioactivity in the column and the wash solution one could estimate the immunoreactivity of the antibody. By this method it was found that 71.1% of radiolabeled 88BV59-PAA was immunoreactive indicating that conjugation of PAA to 88BV59 did not affect the immunoreactivity of the native antibody.

Synthesis of PEI-LiLo/PEI-DTPA

Poly(ethyleneimine) (PEI) Polysciences, was purified 3 times by precipitation in 10 fold excess of acetone and dried under vacuum at 40° C. overnight. LiLo-amino acid was prepared using the procedure described elsewhere (12). PEI was reacted with Br-LiLo to obtain PEI-LiLo as described in FIG. 7.

Preparation of 1,3-Bis[N-[N-(2-aminoethyl)-2-aminoethyl]-2-aminoacetamido]-2-[4-aminoacetamidobenzyl]propane-N, N,N',N'',N''', N'''',N''''',N''''''-octaacetic acid (Br-LiLo)

1,3-Bis[N-[N-(2-aminoethyl)-2-aminoethyl]-2-aminoacetamido]-2-[4aminobenzyl]propane-N,N,N',N'', N''',N'''',N''''',N''''''-octaacetic acid (LiLo-NH2 acid, 100 mg, 0.108 mmole) was dissolved in 7 mL of distilled water. To the solution sodium carbonate (171 mg, 1.62 m mole) was added. Bromoacetyl bromide (130 uL, 1.63 m mole) was dissolved in 7 mL chloroform. LiLo-NH2 acid solution containing sodium carbonate and bromoacetyl bromide in chloroform were mixed and vigorously stirred for 1 hour. The pH of the aqueous layer was adjusted to 2-3 with 4M HCl, and then the water layer was extracted with chloroform until the organic extract was negative to a test of alkylating agents using 4-(p-nitrobenzyl)pyridine. The water layer containing Br-LiLo was lyophilized to a powder and stored at −70° C.

The purified PEI (64.5 mg, 1.53 unit m mole) was dissolved in 1 ml of deionized water. To the solution Br-LiLo (45.1 mg, 0.043 m mole) was added. The pH of the solution was adjusted to 9 with sodium carbonate. The reaction was allowed to proceed at room temperature for 6 hours. The modified PEI was precipitated out in 5 fold excess of acetone for 5 times, dissolved in 300 uL water, and stored at −2° C.

EXAMPLE II

Synthesis of PVP-DTPA A representative chelator, DTPA, was attached to an interacting polymer P1, poly(N-vinylpyrrolidone) using methods illustrated in FIG. 3. Vinyl pyrrolidone/vinyl acetate copolymer was hydrolyzed with NaOH and modified with bromoacetylbromide and treated with aminobenzyl DTPA acid to obtain P(VP-VA)-DTPA (VIII). This copolymer contains 60% of pyrrolidone units. For simplicity, we will call this copolymer PVP-DTPA.

The above methods can also be used to link other chelates such as LiLo, HETA, DOTA and etc. Also, other interacting polymers can be used instead of PVP (FIG. 7).

The biological targeting entity, in this case, an anti-cancer antibody, is attached to another interacting polymer, P2, poly(acrylic acid). In this case the antibody is modified using SATA, and the modified antibody is attached to PAA using coupling agents (FIG. 7). One could use other polymers, such as poly(methacrylic acid). Also, other proteins, such as enzymes and receptors can also be used instead of monoclonal antibodies.

Bifunctional chelating agents such as LiLo and DTPA, which bind to medically useful isotopes such as indium-111 and yttrium-90, were attached to one of the interacting polymer pair PVP. The resultant product is novel. The product has been characterized by analytical methods. Procedures are also given for attachment of chelates to yet another polymer, PEI. The reagents by themselves are useful to prepare high specific activity metal chelates, which will have immense use in diagnostic and therapeutic applications.

Using the methods described in the examples a person trained in the art will be able to attach other compounds, such drugs and toxins, to polymers.

We describe in detail the methods for attaching polymers to proteins, such as monoclonal antibodies. In addition, using methods described in the literature using different kinds of linkers and other reagents, one will be able to obtain easily protein-polymer conjugates for use according to the invention.

By coupling the interacting synthetic polymers to monoclonal antibodies and chelating agents, we have demonstrated that the pairs interact well even after modification. We have confirmed the occurrence of these interactions by employing viscosity studies.

Viscosity studies

One way to determine the extent of interaction between two polymers is the use of viscosity measurements. If two solutions containing two different entities do not interact when they are mixed, the macromolecular viscosity of the solution will often increase. However, if there is high binding between the two polymers due to hydrogen bonding, hydrophobic forces or coloumbic interactions, the viscosity of the solution will decrease indicating the decrease in the entropy of the solution mixture. We demonstrated that the viscosity of a solution mixture containing antibody coupled PAA and PVP-DTPA decreases markedly compared with the viscosity of PAA or PVP-DTPA alone.

It has been reported in the literature that the viscosity of the solution is lowered when the complexation occurs between two polymers in aqueous solution (10). The mixing ratio at which the specific viscosity is at a minimum is considered to be the composition of the formed complex. Our viscosity measurements were carried out with the following polymer pairs:

A: Poly(N-vinylpyrrolidone) (PVP, Mw 360,000), Poly (acrylic acid) (PAA, Mw 90,000)

Figure 9:
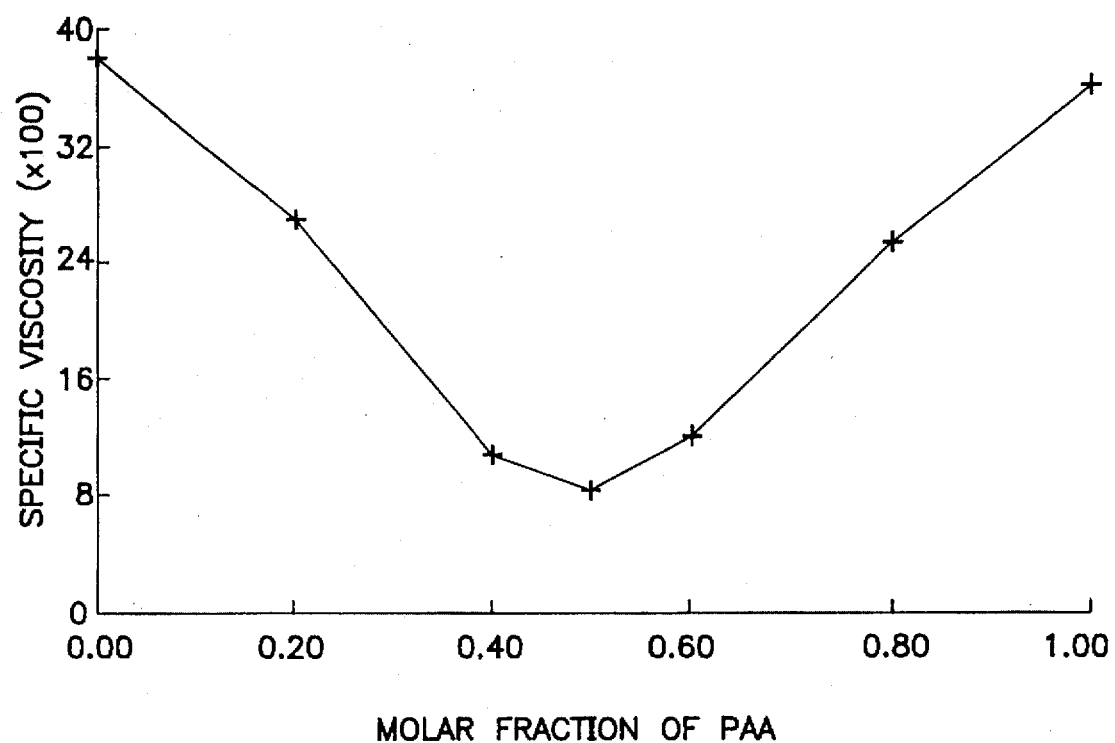
FIG. 9 illustrates the viscosity studies of PVP and PAA.

The overall concentration of ([PVP]+[PAA]) was kept constant at 0.0222 unit mole/l. The specific viscosity was obtained for a series of solutions with different unit molar ratios of PAA to PVP. The specific viscosity of the solutions vs. unit molar fraction of PAA was plotted (FIG. 9). A minimum point and decrease of the viscosity indicated the complex formation between PAA and PVP. The composition of the complex was 1:1 unit molar ratio. The pH of the complex solution showing the minimum point was found to be 4.6. The more concentrated solutions resulted in the formation of precipitates. The viscosity of the polymer solutions were measured in buffer solutions (Citric acid-$Na_2HPO_4$ buffers, 0.05–0.1 M, pH 4.0, 5.0, 6.0 and 7.0). The decreased viscosity and minimum point were seen for solutions at pH 4.0 and 5.0. The interactions were considerably less at pH 6.0 and 7.0.

B: Viscosity Study Control (PVP, Mw 10000)

Figure 11:
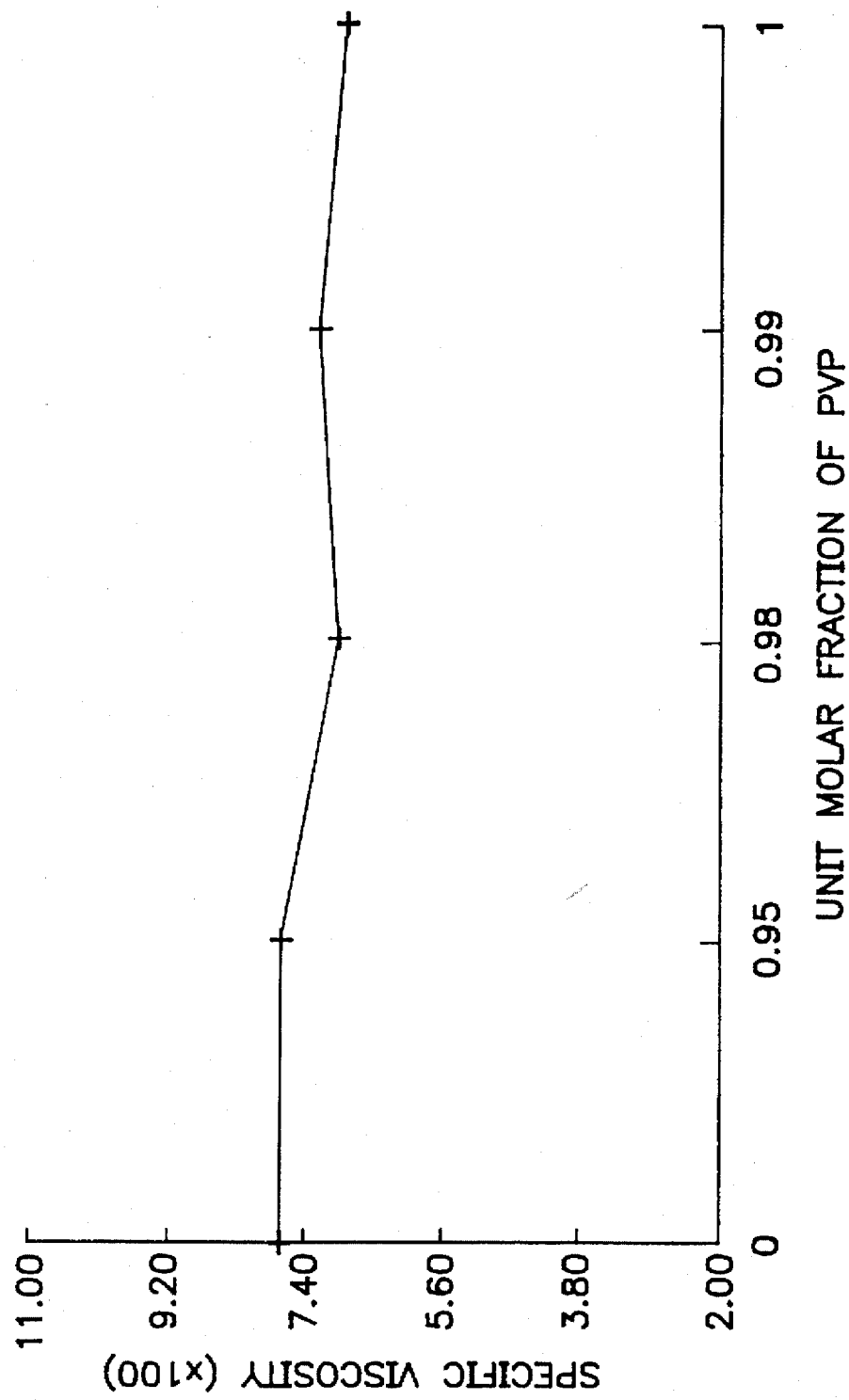
FIG. 11 illustrates the viscosity studies of PVP and 88BV59 MoAb.

The concentration of PVP was $2\times10^{-3}$ mole/l. The concentration of 88BV59 was $4.5\times10^{-5}$ mole/l. Both components were in 5 mM sodium acetate buffer (pH 5.0). The plot (FIG. 11) of specific viscosity vs. molar fraction of PVP showed no lowering of viscosity when the PVP and 88BV59 solutions were mixed indicating no complex formation between MoAb and PVP in the absence of PAA.

3. PVP-DTPA (Mw of PVP 8,000) and 88BV59-PAA/ 16.88-PAA (Mw of PAA 5,000)

Figure 10:
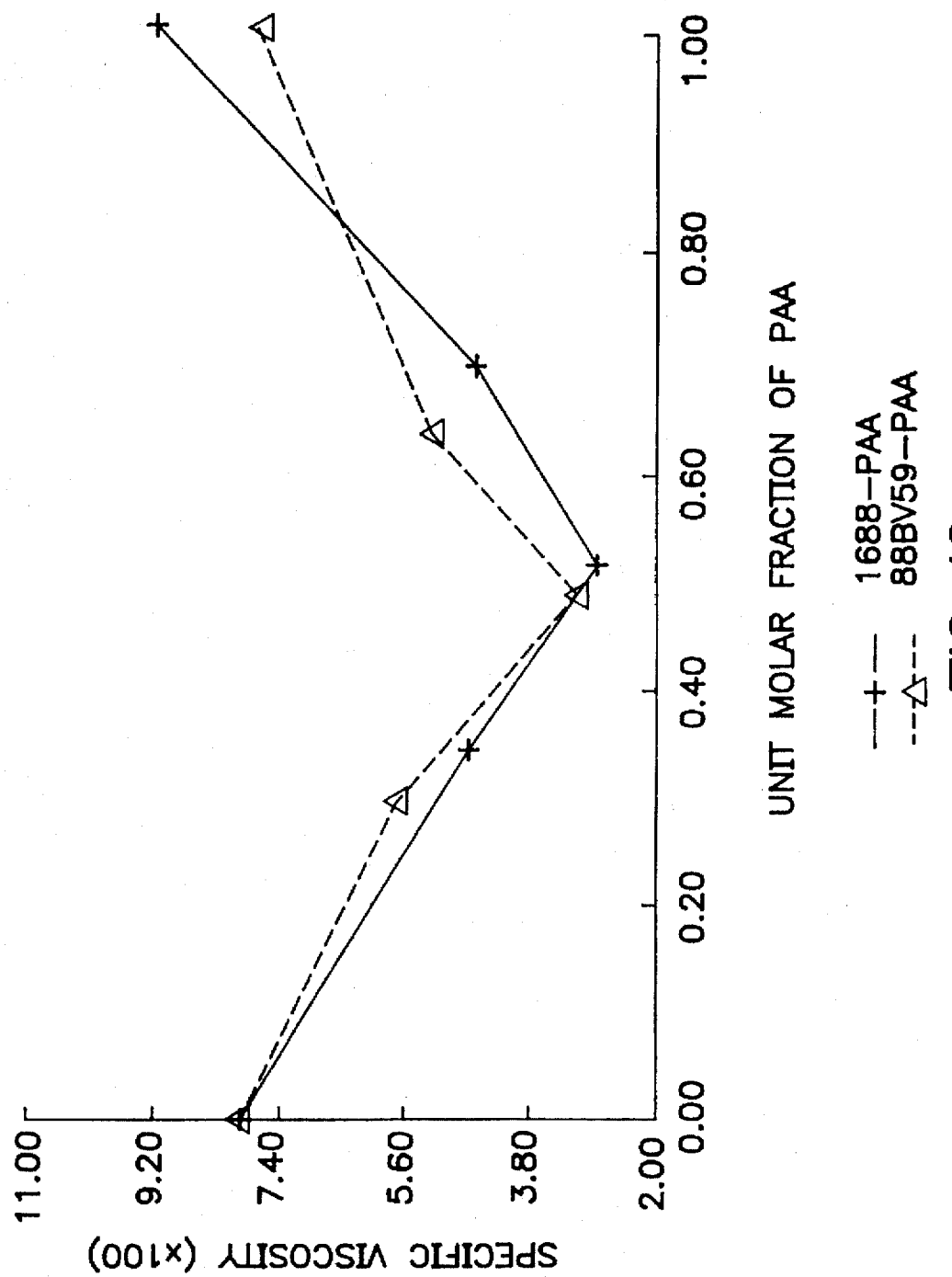
FIG. 10 illustrates the viscosity studies of PVP-DTPA and MoAb-PAA.

The overall concentration of PVP unit in PVP-DTPA and PAA in 88BV59-PAA was kept constant at 3 units mmole/l. Both conjugates (PVP-DTPA and 88BV59-PAA) were in 5 mM sodium acetate (pH 5.0). The specific viscosity was plotted against unit molar fraction of PAA (FIG. 10). This figure showed the lowering of viscosity of mixed solutions and a minimum around the 1:1 unit molar ratio of PVP to PAA, indicating the formation of the complex of PVP-DTPA and 88BV59-PAA. The specific viscosities of PVP-DTPA and 16.88-PAA were measured under similar conditions (as for PVP-DTPA and 88BV59-PAA) and showed a minimum around 1:1 molar ratio of PVP to PAA. This indicates the formation of the complex between PVP-DTPA and 16.88-PAA (FIG. 10).

4. Poly(ethyleneimine) (PEI) and poly(methacrylic acid) (PMAA) (PEI Mw 50,000–100,000, PMAA Mw 100,000)

Figure 12:
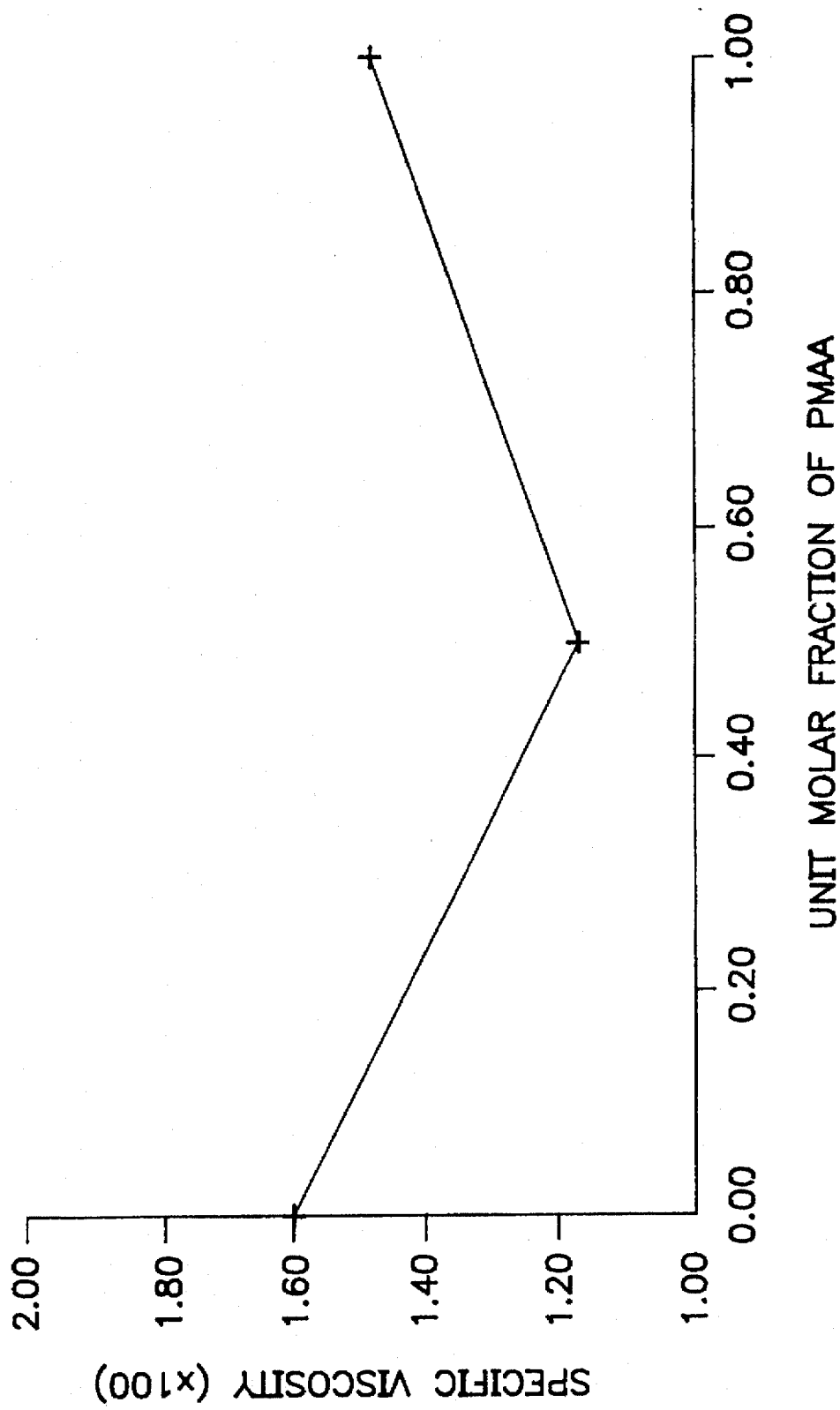
FIG. 12 illustrates the viscosity studies of PEI and PMAA.
Figure 13:
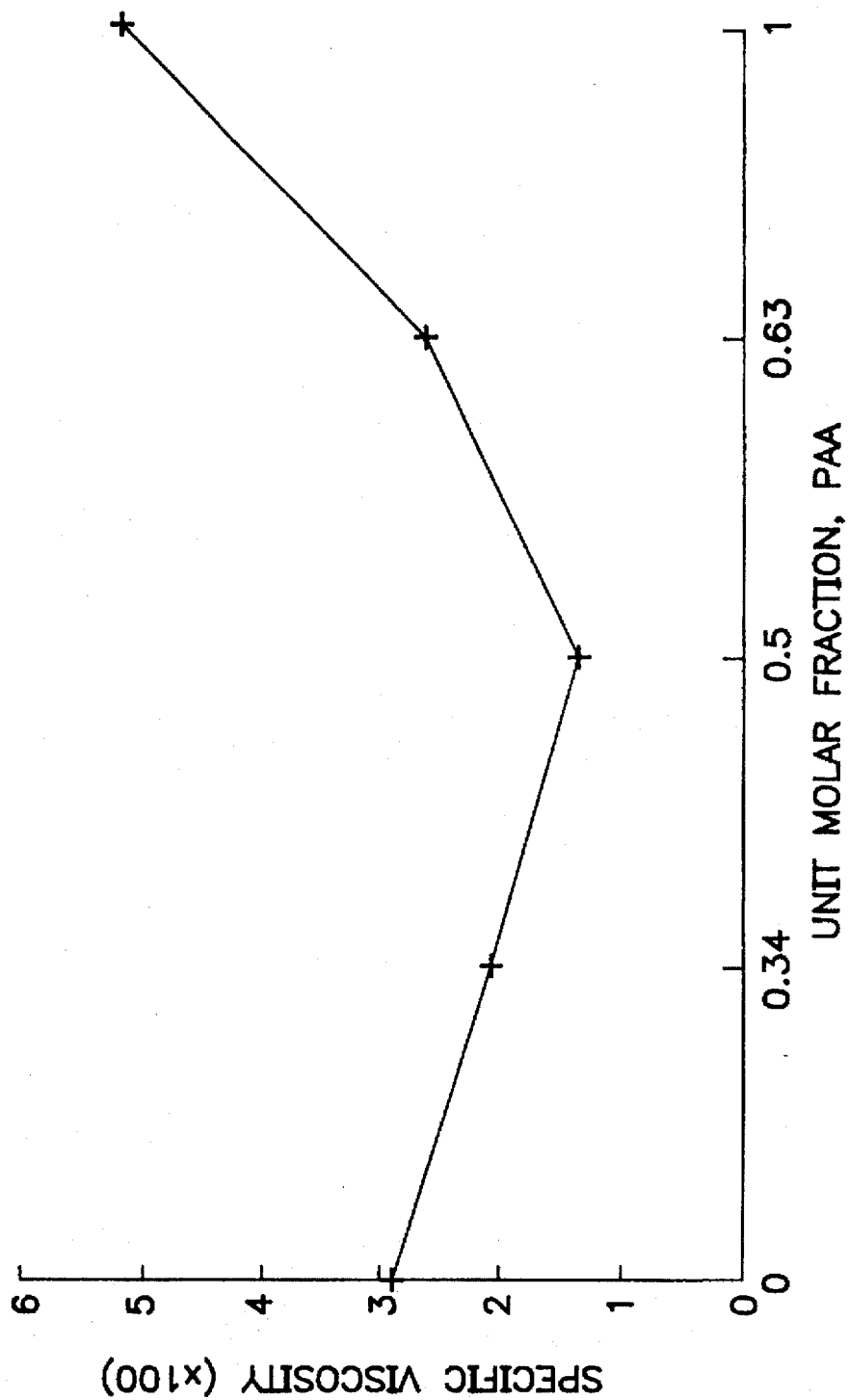
FIG. 13 illustrates the viscosity studies of PEI-DTPA and 88BV59-PAA.

Both PEI and PMAA were dissolved in 0.075M saline solution. The overall concentration was kept at 0.00555 unit mole/l. The plot (FIG. 12) of specific viscosity vs. unit molar fraction of PMAA showed a minimum around 1:1 unit molar ratio. The pH of the solution was 6.7. More concentrated aqueous solutions of PEI and PMAA resulted in precipitates upon mixing the solutions at pH 8.3. The complexation between antibody conjugate 88BV59-PAA and PEI-DTPA was also confirmed by carrying out viscosity measurements. A 1:1 complexation was found to occur between these two polymers as shown in FIG. 13. This experiment was carried out at pH 7.

The interaction between the polymer pairs depends on several factors such as pH, the concentration of the polymer solutions, ionic strength, temperature and nature of the solvent. For PAA and PVP pairs, complex formation occurs at pH 5 or below, and the higher the concentration, the stronger the interaction. The interaction between PEI and PMAA is stronger compared to that between PAA and PVP, especially at higher pH. The pH of the complex solution of PEI and PMAA showing the minimum viscosity (FIG. 12) was 6.7.

This invention can be used in practice to treat cancer patients as follows:

Step 1: Administer antibody coupled PAA to the patient. Allow the conjugate to localize to the site of tumor. In order to accelerate the process of clearance, if necessary, administer PVP. This will remove the circulating PAA conjugate, if any.

Step 2: One to 4 days post administration of MoAb-PAA/ PVP as described in step 1, administer radiolabeled PVP-DTPA. Depending on the purpose, the isotope to be used will be Tc(99m) and In(111) for diagnosis or Y(90), Re(186) or I(131) for therapy. One to 4 days post administration of PVP-DTPA obtain gamma camera images to determine the optimum imaging time, and the radiation dose delivered to tumor and normal organs.

EXAMPLE III

Animal Studies:

Tissue biodistribution and tumor targeting experiments are carried out using antibody coupled polymers and polymer chelates in mice as described earlier (12). Tumor retention studies are carried out in athymic mice bearing 0.5–1.5 cm diameter xenografts of the THO colon carcinoma prepared from enzymatically dissociated cells or LS174t cells. Six-to-eight week old athymic mice (Balb/c, nu/nu) are injected in the tail vein with 10–1000ug of polymer coupled antibody (88BV59-PAA) in about 0.1 to 0–5 mL of saline solution. The antibody conjugate is allowed to localize at the site of tumor. The conjugate that does not bind to tumor clears off from circulation within 2 days. After 1 to 5 days post administration of the conjugate 88BV59-PAA, indium-111 labeled polymer chelate (PVP-LiLo or PEI-LiLo, 5-500 ug, 5-500 uCi) is administered to the mice in about 0.5 mL of saline solution. Animals are sacrificed at intervals from 15 min. to 48 hours after administration. Blood is collected and sera counted for indium-111 at periodic intervals. Tissues such as liver, spleen, bone, kidney are excised, weighed and counted. Tumor targeting is determined by determining the mass of tumor and amount of radioactivity present by counting the same.

EXAMPLE IV

Human Studies:

Multi step tumor targeting in humans can be demonstrated using methods described in the art. In clinical trials, polymer conjugated human monoclonal antibody (88BV59-PAA, 1–20 mg) is injected intraperitoneally in ovarian cancer patients in approximately 0.5 liter of saline solution. There is rapid localization of the human monoclonal antibody onto peritoneal tumor lesions. The antibody portion that does not bind to tumor penetrate into the blood pool and clear off from the circulation within 1–2 days. One to five days post administration of the antibody, indium-111 labeled polymer chelate (PEI-LiLo or PVP-LiLo, 0.1–5.0 mg, 0.5–5.0 mCi) is injected intraperitoneally in about 0.5 to 1.0 liter of saline solution. One to four hour post administration of radioactive polymer chelate, planar gamma camera and SPECT images of the patient are obtained to confirm the localization of the isotope at the tumor site. Additional images are also obtained up to 2 days post administration of radioactive dose in order to determine the optimum imaging time.

In patients where sufficient tumor localization is observed, the above protocol can be repeated using polymer chelate attached to therapeutically useful beta emitting isotope yttrium-90.

References

1. "Water Soluble Synthetic Polymers" by Philip Molyneux, Volume II, pages 159–162, 1983, John Wiley Edition, New York.
2. R. Subramanian and C. F. Meares, "Bifunctional Chelating Agents for Radiometal Labeled Monoclonal Antibodies", in 'Cancer Imaging with Radiolabeling Antibodies', D. M. Goldenberg, (Ed.,), Kluwer Academic, Boston, p.183–200, 1990.
3. a. D. A. Goodwin, Antibody, Immunoconjugates, Radiopharmaceuticals, 4, 427–434, 1991.
   b. Human Monoclonal Antibodies: Application in Radioimmunotherapy, J. L. Klein, R. L. DeJager, J. C. J. Stiekema, M. V. Haspel, N. P. Pomato, R. Subramanian, and M. G. Hanna, Jr., in 'Cancer Therapy with Radiolabeled Antibodies', D. M. Goldenberg, Ed., CRC Press, Baca Raton, Fla., 1995.
4. H. Sands, Antibody, Immunoconjugates and Radiopharmaceuticals, 4, 245–272, 1988.
5. S. P. Kramer, L. E. Goodman, H. Dorfman, R. Solomon, A.M. Rutenbeurg, E. Pineda, L. L. Nason, A. Ulfohn, S. D. Gaby, D. Bakal, C. E. Williamson, J. I. Miller, S. Sass, B. Whitten and A. M. Seligman, J. Natl. Cancer Inst., 31, 297–326, 1963.
6. S. Udenfriend, S. Stein, P. Bohlen, W. Cairman, W. Leimgruber, and M. Weigele, Science, 178, 871–872, 1972.
7. T. Kaneko, D. Willner, I. Monkovic, J. O. Knipe, G. R. Braslawsky, R. S. Geenfiled, and D. M. Vyas, Bioconjugate Chem, 2, 133–141, 1991.
8. R. Julian, S. Duncan, P. D. Weston and R. Wrigglesowrth, Analytical Biochemistry, 132, 68–73, 1983.
9. G. L. Ellman, Arch. Biochem. Biophys., 82, 70, 1959.
10. a. E. Tsuchida, Y. Osada, Makromol. Chem., 175, 593, 1974.
    b. R. Subramanian and P. Natarajan, Journal of Polymer Science, Polymer Chemistry Edition, 22, 437–451, 1995.
    c. R. Subramanian and P. Natarajan, Journal of Polymer Science, Polymer Chemistry Edition, 17, 1855–1860, 1979.
11. M. V. Haspel, R. P. McCabe, N. Pomato, N. J. Janesch, J. V. Knwolton, L. C. Peters, H. C. Hoover, Jr., and M. G. Hanna, Jr., Cancer Res., 45, 3951–3961, 1985.
12. R. Subramanian, J. Colony, S. Shaban, H. Sidrak, M. V. Haspel, N. Pomato, M. G. Hanna, Jr., and R. P. McCabe, Bioconjugate Chem., 3, 248–255, 1991.
13. D. A. Goodwin, C. F. Meares, M. J. McCall, M. McTigue, and Chaovapong, W. Pretargeted immunoscintigraphy of murine tumors with $^{111}$In labeled bifunctional haptens, Journal of Nuclear Medicine, 29: 226–234, 1988.
14. J. Le Doussal, A. Chetanneau, A. Gruaz-Guyon, M. Martin, E. Gautherot, P. A. Lehur, J. F. Chatal, J. Barbet, M. Delaage and J. Barbet, Bispecific monoclonal antibody-mediated targeting of an Indium-111-labeled DTPA dimer to primary colorectal tumors: pharmacokinetics, biodistribution, scintigraphy and immune response, Journal of Nuclear Medicine, 34: 1662–1671, 1993.

We claim:

1. A method for targeting active agents to target sites, comprising providing two polymers that have binding affinity for each other, coupling a targeting agent to the first of the polymers to form a targeting agent-polymer conjugate, coupling an active agent to the second of the polymers in the pair to form an active agent-polymer complex, administering the targeting agent-polymer conjugate to a subject, permitting the conjugate to localize to a target tissue for which the targeting agent has affinity, administering the active agent-polymer complex to the subject, and permitting the complex to bind to the localized targeting-agent polymer conjugate, whereby the active agent becomes localized to the target tissue, wherein the targeting agent is an antibody or an antigen binding fragment having binding specificity for a tumor associated antigen and retaining that specificity in the targeting agent-polymer conjugate, wherein the active agent is selected from the group consisting of a radiometal, a radiohalogen, a metal with magnetic properties and fluorescent metal, and wherein the polymers are selected from the group consisting of poly (N-vinyl pyrrolidone), poly (ethyleneminine) and ply (acrylic acid).

2. The method of claim 1, wherein the subject is a mammal.

3. The method of claim 1, wherein the active agent comprises a chelator.

* * * * *